United States Patent [19]

Sawatsky

[11] 4,258,437

[45] Mar. 31, 1981

[54] EYE SHADE AND METHOD OF PRODUCING EYE SHADES

[76] Inventor: Henry Sawatsky, R.R. #4, Brampton, Ontario, Canada

[21] Appl. No.: 29,120

[22] Filed: Apr. 11, 1979

[30] Foreign Application Priority Data

Jan. 30, 1979 [CA] Canada .................................... 320497

[51] Int. Cl.³ .............................................. A61F 9/04
[52] U.S. Cl. ........................................... 2/12; 2/192
[58] Field of Search ............... 2/12, 171, 171.1, 192, 2/195, 200

[56] References Cited

U.S. PATENT DOCUMENTS

| | | | |
|---|---|---|---|
| 1,631,210 | 6/1927 | Johnson | 2/12 |
| 1,763,899 | 6/1930 | McClay et al. | 2/12 |
| 2,033,691 | 3/1936 | Douglass | 2/12 X |
| 2,112,916 | 4/1938 | Linden | 2/12 X |
| 2,545,097 | 3/1951 | Lucas | 2/12 |
| 2,988,743 | 6/1961 | Wagenfeld | 2/12 |

FOREIGN PATENT DOCUMENTS

| | | | |
|---|---|---|---|
| 1025669 | 1/1953 | France | 2/12 |
| 175468 | 8/1935 | Switzerland | 2/12 |
| 180805 | 2/1936 | Switzerland | 2/12 |

*Primary Examiner*—Peter P. Nerbun
*Attorney, Agent, or Firm*—Burgess, Ryan and Wayne

[57] ABSTRACT

An eye shade and method of producing an eye shade are disclosed. The eye shade comprises a bill member with a curved inner edge and a flange portion upstanding from the inner edge. A rim band or member with a straight lower edge is secured to the flange preferably by spot welding, and upon the rim band being bent about a vertical axis the bill portion is curved about a vertical axis and a downwardly inclined axis. The bill and rim portions are preferably molded in a planar form of flexible plastic. At this stage, if desired, they may be printed. The securement of the bill and rim may be by spot welding. Perspiration and elastic head bands are then mounted on the rim.

9 Claims, 5 Drawing Figures

U.S. Patent
Mar. 31, 1981
4,258,437
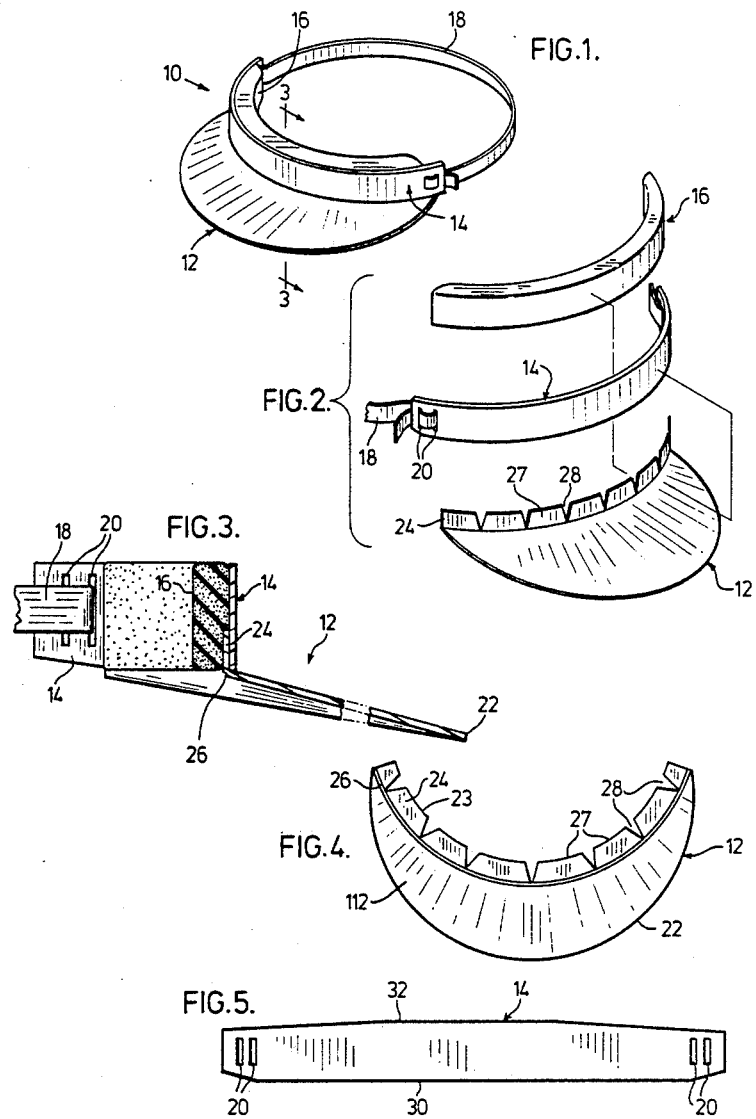

EYE SHADE AND METHOD OF PRODUCING EYE SHADES

This invention relates to eye shades and a method of producing such eye shades as worn, for example, for golfing, sailing, tennis and other out of doors activities.

Eye shades or sun visors which can be used in out of doors activities comprise a horizontally projecting bill part or shade member which is worn at a convenient level above the eyes of the wearer to shade the eyes. The shade is held on the head by means of an adjustable strap or the like which encircles the head of the wearer. These eye shades must be lightweight and comfortable to the wearer when worn.

Various designs have been proposed in the past to provide such eye shades; however, there exists the need for an eye shade which is readily accepted by the market and which can economically be produced in large quantities.

These structures of the prior art have had limited appeal because the designs, particularly integrally molded structures, can only be provided with decoration on flat portions or added by way of adhesive or sewing.

It is an object of the invention to provide an eye shade which is of particularly lightweight design.

It is also an object of the invention to provide an eye shade which is of sturdy construction.

It is further an object of the present invention to provide an eye shade which is readily furnished with a decorative printing at least on the shade member thereof.

In accordance with the present invention there is provided an eye shade for wear on the head which comprises a bill member, and a rim member, said bill member including a substantially horizontally extending bill portion having a curved inner edge and curved about a first substantially vertical axis and a second axis downwardly inclined with respect to said first-mentioned axis, and an upstanding flange portion; said rim member having a substantially linear lower edge and being connected to said flange portion.

The eye shade may include a perspiration-absorbing strip of material which is secured to the inner surface of the rim band, and preferably includes a band of elastic material for retaining the eye shade on the head of a wearer.

In accordance with the invention there is also provided a method of producing an eye shade assembly, said method comprising the steps of:

molding a flexible plastic material to provide a substantially planar bill member, said bill member having a curved inner edge and flange means extending along at least part of said inner edge and upstandingly foldable therefrom;

and securing a longitudinally extending generally rectangular planar rim band having a substantially linear lower edge to said flange means whereupon bending said rim band around a substantially vertical axis said bill member is curved about said first-mentioned vertical axis and a downwardly inclined second axis.

The foregoing and other objects and advantages of the invention will be further described with reference to the accompanying drawings of an embodiment of the invention, in which FIG. 1 is a general perspective view of an eye shade in accordance with one embodiment of the invention;

FIG. 2 is an exploded, perspective view of the eye shade in accordance with FIG. 1;

FIG. 3 is a cross-section taken along line 3—3 of FIG. 1;

FIG. 4 is a bottom plan view of a bill member for an eye shade in accordance with FIG. 1;

FIG. 5 is a top or bottom plan view of a rim band for an eye shade in accordance with FIG. 1;

With reference to the general view of FIG. 1, an eye shade 10 is comprised of a bill member 12, a rim band 14 and a perspiration-absorbing strip 16, all secured as described later in this description. The eye shade is normally worn around the head as previously mentioned and held by means of an elastic band 18 which is adjustably secured to each end of the rim band 14, such as by insertion in band-receiving slots 20.

The bill member 12, shown in FIGS. 1 through 4, has a generally flat crescent-shaped section 112 when viewed in plan; a forward, horizontally projecting outer edge 22 of generally arcuate form; and an inner edge 23 from which a flange section 24 extends inwardly.

Flange section 24 comprises a plurality of individual flanges 27, which are formed integrally and in the same plane as the crescent-shaped section 112 and are connected hereto by a groove 26. Each flange 27 is separated from its adjacent flange by a V-shaped notch such as 28. V-shaped groove 26 defining the inner edge 23, provided in the lower surface of the shade member, preferably, has a depth of about 0.6 of the thickness of the shade member. Thus, when the shade member has a thickness of 0.005, the depth of the groove is about 0.003 of an inch.

It will be readily appreciated that the flange section 24 can assume an upstanding, generally vertical position as is indicated in FIG. 3 by being bent up about the groove 26, which forms a line of weakness in the material. The desired curvature in the flange section 24, i.e., the curvature to permit wearing of the eye shade 10 by a user, is provided by the V-shaped notches 28 in the flange section 24.

The rim band 14, shown in detail in FIG. 5, is of generally longitudinal, rectangular configuration with a linear lower edge 30, which may be slightly chamfered at the respective vertical edges. The upper longitudinal edge 32 may be curved or smoothed, when viewed in plan. The rim band in accordance with the embodiment can have a thickness of about 0.005 inches.

The perspiration-absorbing strip 16 can be of any suitable material, such as sponge, synthetic foam, or the like and of a suitable thickness and length to provide comfort to the wearer.

The elastic band 18 is readily provided by an elastic webbing of suitable length and width.

Preferably, the shade member 12 and the rim band 14 are molded or cut out of a suitable flexible plastic material which takes printing, in a flat or planar form.

After printing, the rim band 14 is centered over the center of the flange section 24 and the individual flanges 27 are secured by spot-welding to the rim band 14. When the spot-welding is completed and the rim band 14 bent into a circular form, the bill member 12 assumes the bilateral curvature as indicated in FIG. 1. Then the strip 16 of perspiration-absorbing material is affixed, for example, by gluing, to cover the overlapping joint of flange section 24 and rim band 14.

The assembly as shown in FIG. 1 is readily completed by insertion of the ends of an elastic band 18 with its ends in the slots 20 of the respective ends of the rim band 14.

The invention provides for a number of important advantages. Thus, the components of the eye shade which are normally subjected to the greatest wear are economically produced by molding. Molding will provide parts of accurate dimensions leading to an assembly which is of particularly pleasing appearance. The molding of the shade member and rim band provides components with substantially planar surfaces which are readily imprinted over their entire surfaces instead of a limited area as previously.

The molding of the shade member with lines of weakness such as the groove to permit formation of an upstanding rim provides an eye shade which is particularly comfortable when worn by a user. This comfort is augmented by the correct curvature achieved on spot-welding of the rim band to the flange portion of the shade member.

It will be appreciated that modification can be made to the embodiments described. Thus, it will be possible to make use of a groove which is not continuous, i.e., an intermittent scoring, for the line of weakness defining the flange on the shade member. The flange means may be provided by a plurality of projections to present a large enough surface area to secure the rim band, and instead of the elastic band, a cap part with an elastic band can be provided to retain the eye shade on the wearer's head.

Other modifications and variations can be made without departing from the spirit and scope of the appended claims.

The embodiments of the invention in which an exclusive property or privilege is claimed are defined as follows:

1. An eye shade for wear on the head and formed from flexible plastic material comprising:
   a bill member; and
   a rim member;
   the bill member including a portion having a curved inner edge and which is curved within a plane perpendicular to a first substantially vertical axis and a curved outer edge which extends along a line below said plane;
   the bill member having an integrally formed flange portion therefrom, said flange portion comprising a plurality of flange elements spaced apart by V-shaped slots said V-shape slots being present during assembly of the eye shade when the flange portion and the bill member are oriented in the same plane;
   said flange portion being delineated from the body of the bill member by a groove forming the line of the curved inner edge;
   the rim member having a substantially linear horizontal lower edge that extends substantially within a single plane and being connected to each of said flange elements by spot welding;
   a longitudinal strip of perspiration-absorbing material being secured to the shade along the curved edge.

2. Eye shade in accordance with claim 1 further including means for retaining the eye shade on the head of the wearer.

3. Eye shade in accordance with claim 1 wherein said bill member and said rim planar in form prior to assembly.

4. Eye shade in accordance with claim 3, wherein at least the bill member includes decorative printing at least on the upper surface thereof.

5. An eye shade as claimed in claim 1 wherein said bill portion has an outer edge and said outer edge is curved and describes an arc intersecting with the arc of said inner edge.

6. Method of producing an eye shade assembly, said method comprising the steps of:
   molding a flexible plastic material to provide a substantially planar bill member, said bill member having a curved inner edge and flange means extending along at least part of said inner edge;
   providing a groove on the bill member extending a predetermined distance from the curved inner edge to provide an flange;
   providing V-shaped slots in said flange to divide it into a plurality of flange elements including slots permitting curving of said flange along the curved edge;
   and securing a longitudinally extending generally rectangular planar rim band having a substantially linear lower edge to said flange whereupon bending said rim band around a substantially vertical axis, a curved inner edge of said bill member is curved within a plane perpendicular to said vertical axis and a curved outer edge of said bill member extended along a line below said plane.

7. Method in accordance with claim 6, wherein said rim band is secured to said upstanding flange by spot welding.

8. Method in accordance with claim 6, further including the step of printing at least the upper surface of the bill member when in a planar form.

9. Method in accordance with claim 6, further including the step of imprinting a decoration on the outer surface of said rim band when in a planar form.

* * * * *